US006641039B2

(12) United States Patent
Southard

(10) Patent No.: US 6,641,039 B2
(45) Date of Patent: Nov. 4, 2003

(54) SURGICAL PROCEDURE IDENTIFICATION SYSTEM

(75) Inventor: Michael A. Southard, Arlington, TX (US)

(73) Assignee: Alcon, Inc., Hunenberg (CH)

( * ) Notice: Subject to any disclaimer, the term of this patent is extended or adjusted under 35 U.S.C. 154(b) by 0 days.

(21) Appl. No.: 10/103,382

(22) Filed: Mar. 21, 2002

(65) Prior Publication Data

US 2003/0178488 A1 Sep. 25, 2003

(51) Int. Cl.[7] ............................................. G06F 17/60
(52) U.S. Cl. ...................................................... 235/385
(58) Field of Search ............................... 235/385, 383, 235/462.13; 283/74, 81; 206/379, 363, 370; 705/28, 29

(56) References Cited

U.S. PATENT DOCUMENTS

| 4,833,306 A | * | 5/1989 | Milbrett ...................... 235/375 |
| 4,844,259 A | * | 7/1989 | Glowczewskie et al. ..... 206/370 |
| 5,048,870 A | | 9/1991 | Mangini et al. |
| 5,283,943 A | * | 2/1994 | Aguayo et al. ................ 29/701 |
| 5,845,264 A | * | 12/1998 | Nellhaus ....................... 705/28 |
| 5,899,674 A | | 5/1999 | Jung et al. |
| 6,005,482 A | * | 12/1999 | Moran et al. ............. 340/568.8 |
| 6,036,458 A | | 3/2000 | Cole et al. |
| 6,059,544 A | | 5/2000 | Jung et al. |
| 6,098,892 A | * | 8/2000 | Peoples, Jr. .................. 235/494 |
| 6,155,975 A | | 12/2000 | Urich et al. |
| 6,238,623 B1 | | 5/2001 | Amhof et al. |
| 6,341,726 B1 | * | 1/2002 | Castanedo et al. ...... 235/462.13 |
| 2001/0006818 A1 | | 7/2001 | Amhof et al. |

FOREIGN PATENT DOCUMENTS

JP    09205291 A  *  8/1997  .......... H05K/13/00

* cited by examiner

Primary Examiner—Diane I. Lee
(74) Attorney, Agent, or Firm—Jeffrey S. Schira

(57) ABSTRACT

A surgical system console having an electronic identification system, such as a bar code scanner, magnetic reader or other optical or magnetic system that works in conjunction with a unique identifier on the surgical pak so as to identify the contents of the pak to the surgical system console control CPU and to print out the contents of the surgical pak on a list.

7 Claims, 5 Drawing Sheets

SURGICAL PROCEDURE IDENTIFICATION SYSTEM

BACKGROUND OF THE INVENTION

This invention relates generally to the field of cataract surgery and more particularly to surgical paks used during the phacoemulsification technique of cataract removal.

The human eye in its simplest terms functions to provide vision by transmitting light through a clear outer portion called the cornea, and focusing the image by way of the lens onto the retina. The quality of the focused image depends on many factors including the size and shape of the eye, and the transparency of the cornea and lens.

When age or disease causes the lens to become less transparent, vision deteriorates because of the diminished light which can be transmitted to the retina. This deficiency in the lens of the eye is medically known as a cataract. An accepted treatment for this condition is surgical removal of the lens and replacement of the lens function by an artificial intraocular lens (IOL).

In the United States, the majority of cataractous lenses are removed by a surgical technique called phacoemulsification. During this procedure, a thin phacoemulsification cutting tip is inserted into the diseased lens and vibrated ultrasonically. The vibrating cutting tip liquifies or emulsifies the lens so that the lens may be aspirated out of the eye. The diseased lens, once removed, is replaced by an artificial lens.

A typical ultrasonic surgical device suitable for ophthalmic procedures consists of an ultrasonically driven handpiece, an attached cutting tip, and irrigating sleeve and an electronic control console. The handpiece assembly is attached to the control console by an electric cable and flexible tubings. Through the electric cable, the console varies the power level transmitted by the handpiece to the attached cutting tip and the flexible tubings supply irrigation fluid to and draw aspiration fluid from the eye through the handpiece assembly. The disposable portions of the system, such as the cutting tips, fluid tubings, cassette, drapes and sleeves, are generally sold together as a complete unit in the form of a surgical pak.

In use, the ends of the cutting tip and irrigating sleeve are inserted into a small incision of predetermined width in the cornea, sclera, or other location. The cutting tip is ultrasonically vibrated along its longitudinal axis within the irrigating sleeve by the crystal-driven ultrasonic horn, thereby emulsifying the selected tissue in situ. The hollow bore of the cutting tip communicates with the bore in the horn that in turn communicates with the aspiration line from the handpiece to the console. A reduced pressure or vacuum source in the console draws or aspirates the emulsified tissue from the eye through the open end of the cutting tip, the cutting tip and horn bores and the aspiration line and into a collection device. The aspiration of emulsified tissue is aided by a saline flushing solution or irrigant that is injected into the surgical site through the small annular gap between the inside surface of the irrigating sleeve and the cutting tip.

With the advances that have been made in the last few years in digital circuitry, manufacturers are able to design and built surgical instruments that can automatically change the operating parameters to suit special techniques or situations. Operating parameters such as aspiration fluid flow rate and vacuum, irrigation fluid flow rate and pressure and handpiece power and duty cycle can all be preprogrammed for a specific surgeon or surgical procedure. In addition, the various cutting tips, sleeves, tubings and cassettes can be customized to suit the techniques being used by the surgeon. In order optimize the system, it is important that the operating parameters, tips, sleeves, tubings and cassettes all be designed to work together. With the various disposable products that are available today, it is often difficult for the surgeon to know if the operating parameters of the surgical console have been optimized for the contents of the surgical pak being used.

One prior art device illustrated in U.S. Pat. Nos. 5,899,674 and 6,059,544 (Jung, et al.) discloses a surgical cassette having an identification system that can be used by the surgical console to identify the type of cassette being used. Another similar device, illustrated in U.S. Pat. No. 6,036,458 (Cole, et al.), discloses a surgical cassette having an identification system that can be used by the surgical console to identify the type of cassette being used as well as how many times the cassette has been used. None of these references discloses a system wherein the surgical console can identify all of items contained in the surgical pak, and automatically adjust the operating parameters of the system for those contents.

Therefore, a need continues to exist for a system that can identify all of the contents of a surgical pak and automatically adjust the operating parameters of the system for those contents.

BRIEF SUMMARY OF THE INVENTION

The present invention improves upon the prior art by providing a surgical system console having an electronic identification system, such as a bar code scanner, magnetic reader or other optical or magnetic system that works in conjunction with a unique identifier on the surgical pak so as to identify the contents of the pak to the surgical console control CPU and to print out the contents of the surgical pak on a list.

Accordingly, one objective of the present invention is to provide a surgical system having a console with an electronic identification system.

Another objective of the present invention is to provide a surgical system having a console capable of identifying the contents of a surgical pak.

Another objective of the present invention is to provide a surgical system having a surgical pak having contents that are identifiable to the surgical console.

DETAILED DESCRIPTION OF THE INVENTION

Figure 1:
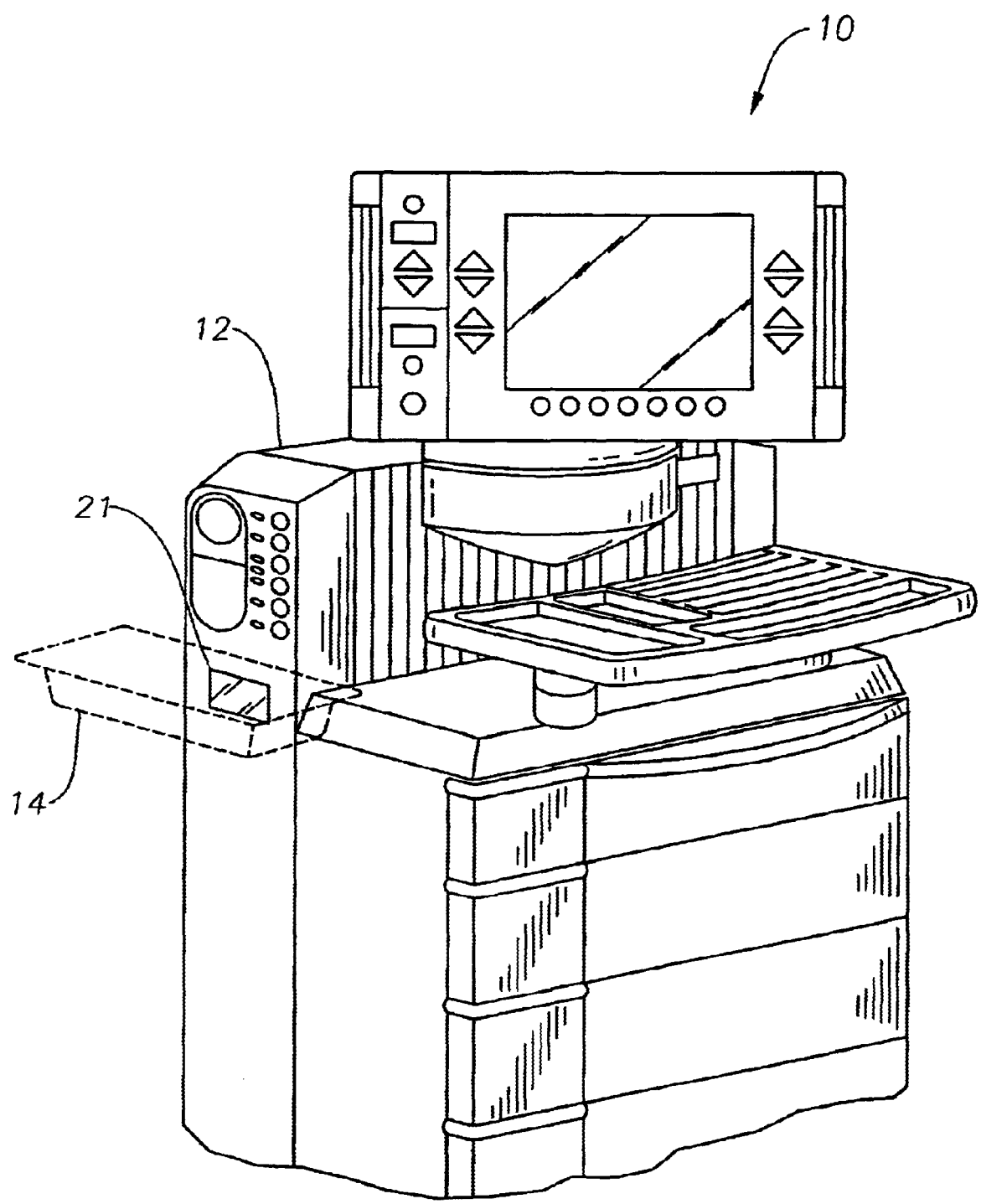
FIG. 1 is a perspective view of a surgical console that may be used with the present invention, showing the surgical pak in phantom.

As best seen in FIG. 1, system 10 of the present invention generally includes surgical console 12 and surgical pak 14.

Figure 2:
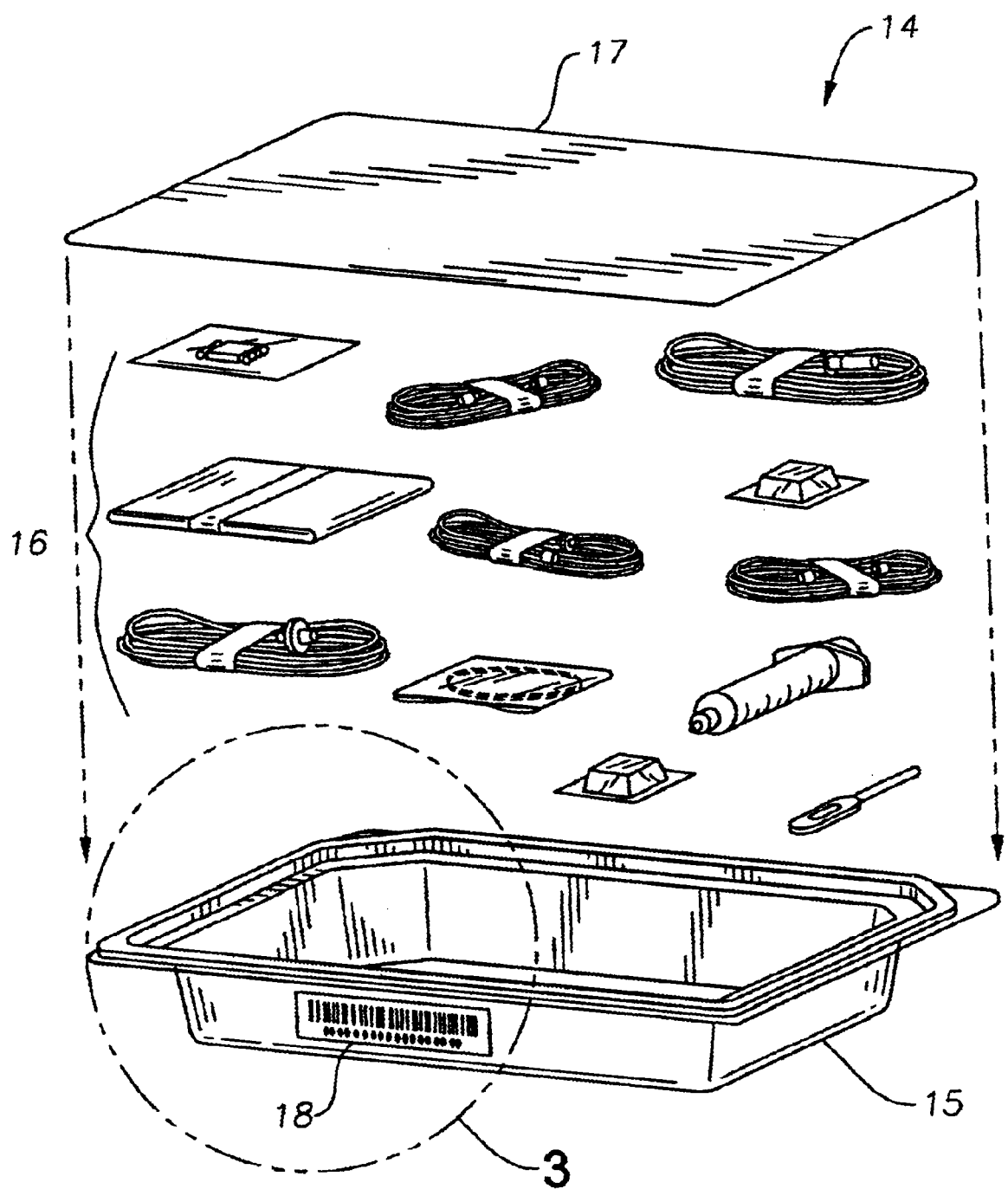
FIG. 2 is an exploded perspective view of a surgical pak that may be used with the present invention showing the various contents of the pak.

Console 12 may be any suitably modified commercially available surgical console, such as the SERIES TWENTY THOUSANDS® LEGACY® or ACCURUS® surgical systems available from Alcon Laboratories, Fort Worth, Tex. Pak 14 may be any suitably modified commercially available surgical pak, such as those sold by Alcon Laboratories, Inc., Fort Worth, Tex. and, as best seen in FIG. 2, may contain any of a variety of components 16 required to perform a particular surgical procedure, such as cutting tips, sleeves, probes, cassettes, tubing sets, syringes, drapes, etc. Alternative paks 14 may contain pharmaceutical, viscoelastic agents or intraocular lenses. Components 16 are kept sterile in tray 15 by lid 17.

Figure 3:
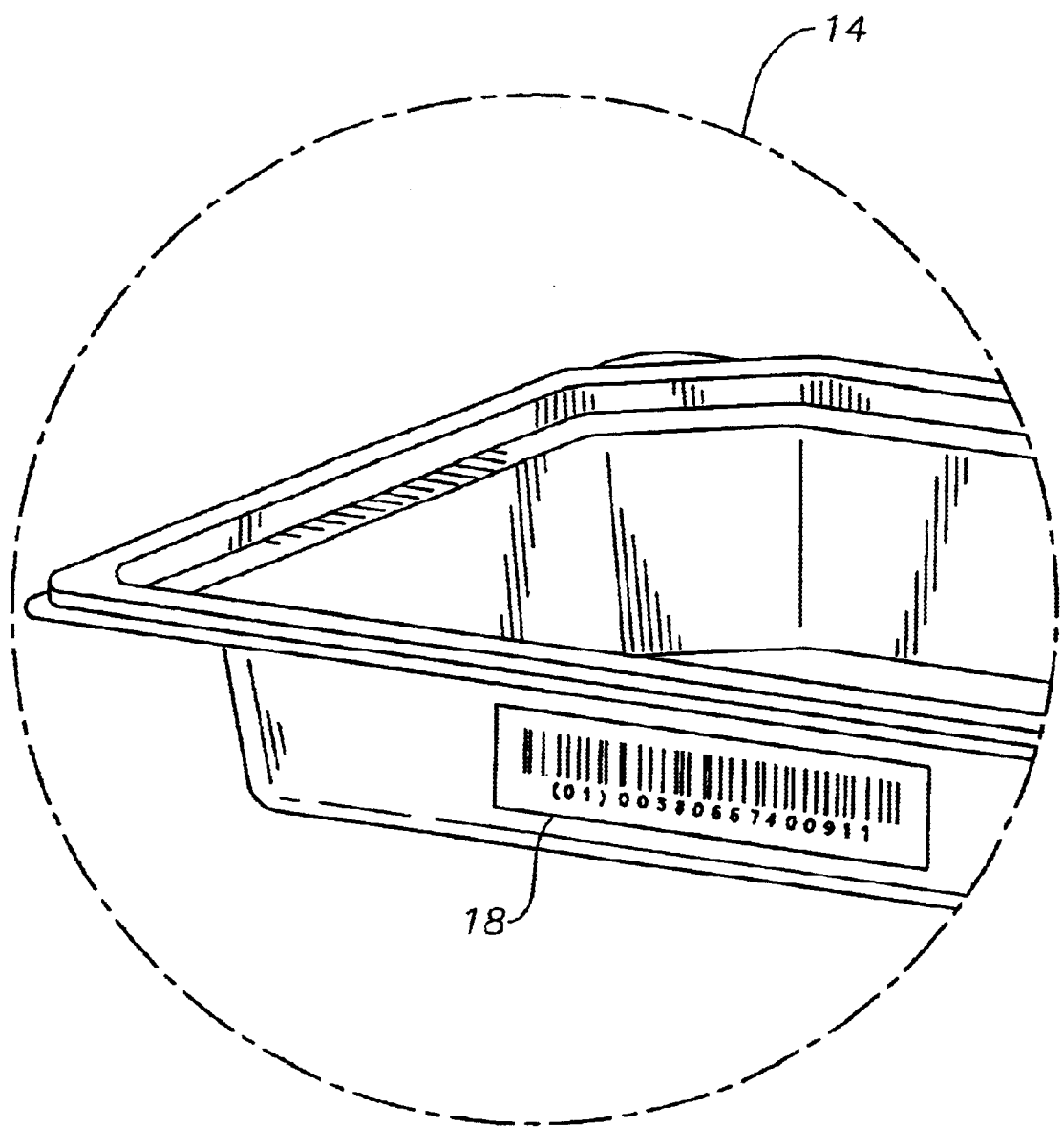
FIG. 3 is an enlarged perspective view of a surgical pak that may be used with the present invention taken at circle 3 on FIG. 2.

As best seen in FIG. 3, pak 14 contains identification device 18, such as a bar code, that identifies the contents of pak 14. Identification device 18 can either be external, such as with a bar code, or internal, such as with a magnetic device. In use, identification device 18 is presented to reader 21 on or connected to console 12. Reader 21 recognizes device 18, identifies pak 14 and components 16 contained in pak 14 and transmits this information to console 12. Console 12 uses this information, under appropriate software control as discussed below, to adjust automatically the operating parameters of console 12 to coincide with components 16 of pak 14 using factory or user programmable settings. Device 18 and reader 20 may be any of a variety of suitable electrical, magnetic or optical devices readily commercially available and well-known in the art.

Figure 4:
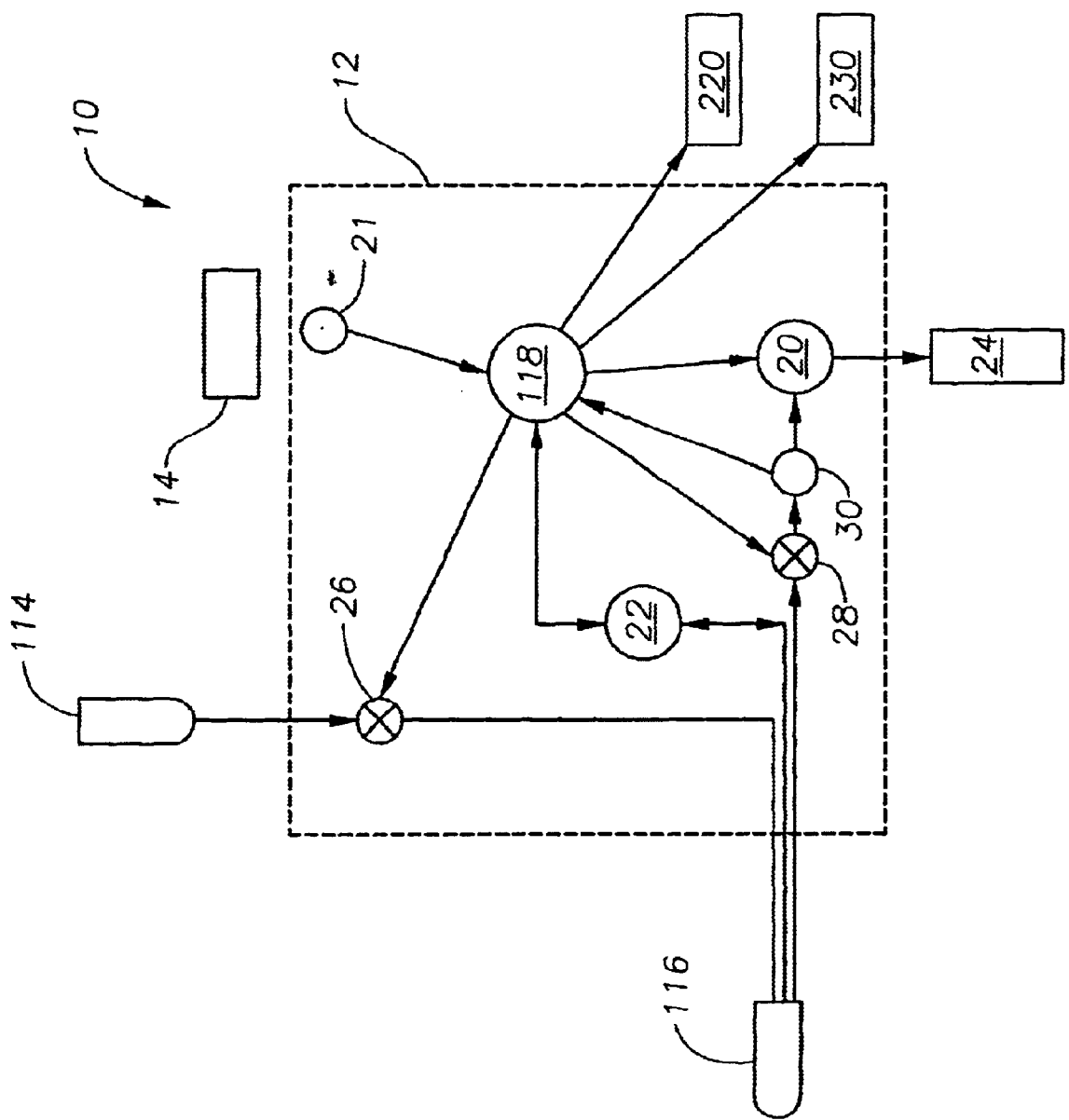
FIG. 4 is a schematic illustration of a surgical system console that may be used with the present invention.

As best seen in FIG. 4, control console 12 generally includes CPU 118, aspiration pump 20, handpiece power supply 22, infusion fluid valve 26, aspiration valve 28 and aspiration pressure sensor 30. Information supplied to CPU 118 from reader 21 is used to control aspiration valve 28, pump 20 and infusion fluid valve 26. CPU 118 also controls the power supplied to handpiece 116 by power supply 22. Aspirated fluid is directed by pump 20 to collection container 24.

Figure 5:
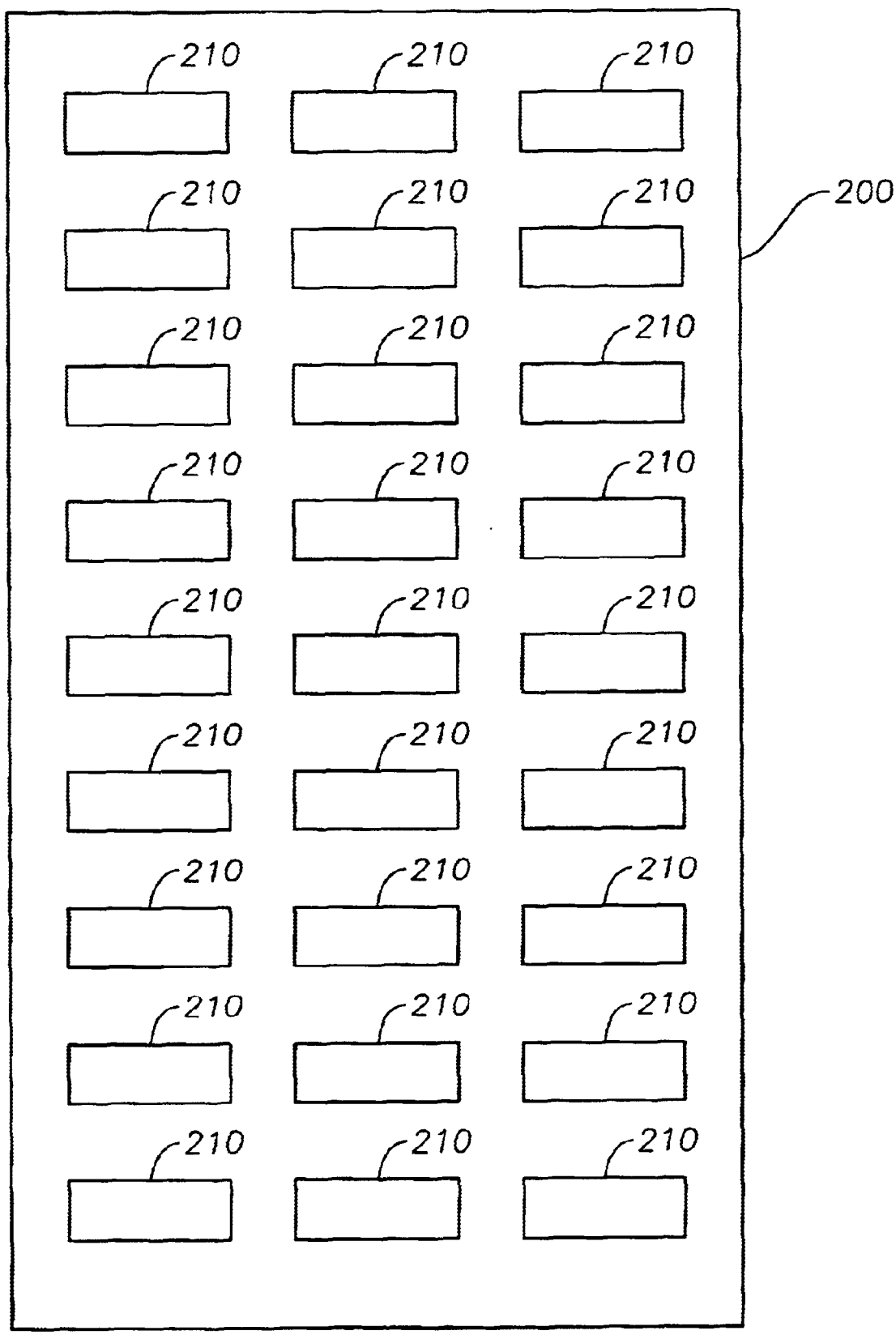
FIG. 5 is an illustration of a printout that may be obtained from the present invention.

In addition, control console 12 can signal printer 220 to print out a list of the contents of pak or paks 14 used during surgery. As seen in FIG. 5, list 200 may be in the form of a series of self-adhesive labels 210 that can be easily detached from list 200 and placed on the patient's medical chart so as to be able to track the various products, lenses, pharmaceuticals, etc. that were used during the surgical procedure. Printer 220 may communicate with control console 12 either via a hardwire connection, or a wireless connection (e.g. BLUETOOTH®).

System 10 may also be used for inventory control/tracking by providing information regarding paks 14 or components 16 being used by the owners of system 10 to inventory management system or software 230, there being numerous inventory management software programs and systems being commercially available and well-known in the art. Inventory management system 230 can be used to re-order paks 14 and/or components 16 automatically. In addition, information such as the serial numbers, lot numbers or other information regarding paks 14 or components 16 can be tracked with system 10 and/or sent directing to the manufacturer(s) of paks 14 and/or componenets 16 through inventory management system 230. Inventory management system 230 may communicate with control console 12 either via a hardwire connection, or a wireless connection (e.g. BLUETOOTH®).

This description is given for purposes of illustration and explanation. It will be apparent to those skilled in the relevant art that changes and modifications may be made to the invention described above without departing from its scope or spirit.

I claim:

1. A surgical procedure identification system, comprising:
   a) an ophthalmic surgical console for performing ophthalmic surgical procedure having a reader;
   b) a surgical pak containing a plurality of components;
   c) an identification device associated with the surgical pak, the identification device capable of being recognized by the reader and providing information about the components contained in the surgical pak to the ophthalmic surgical console; and
   d) a printer connected to the ophthalmic surgical console for printing out a list of the components contained in the surgical pak, the list suitable for inclusion in a patient's medical chart.

2. The surgical procedure identification system of claim 1 wherein the list is a plurality of labels.

3. The surgical procedure identification system of claim 1 wherein the identification device is a bar code and the reader is a bar code scanner.

4. The surgical procedure identification system of claim 1 wherein the connection between the control ophthalmic surgical console and the printer is a wireless connection.

5. A surgical procedure identification system, comprising:
   a) an ophthalmic surgical console for performing ophthalmic surgical procedure having a reader;
   b) a surgical pak containing a plurality of components;
   c) an identification device associated with the surgical pak, the identification device capable of being recognized by the reader and providing information about the components contained in the surgical pak to the ophthalmic surgical console; and
   d) a printer connected to the ophthalmic surgical console for printing out a list of the components contained in the surgical pak, the list suitable for inclusion in a patient's medical chart; and
   e) an inventory management system connected to the ophthalmic surgical console for tracking usage of the surgical pak and/or the components.

6. The surgical procedure identification system of claim 5 wherein the identification device is a bar code and the reader is a bar code scanner.

7. The surgical procedure identification system of claim 5 wherein the connection between the control ophthalmic surgical console and the printer is a wireless connection.

* * * * *